United States Patent
Bui et al.

(10) Patent No.: US 8,551,461 B2
(45) Date of Patent: *Oct. 8, 2013

(54) MOISTURIZING AND SHINE-IMPARTING EMULSION LIP COMPOSITIONS

(75) Inventors: Hy Si Bui, Piscataway, NJ (US); Mohamed Kanji, Edison, NJ (US); Luis Ortega, Englewood, NJ (US)

(73) Assignee: L'Oreal, Paris (FR)

( * ) Notice: Subject to any disclaimer, the term of this patent is extended or adjusted under 35 U.S.C. 154(b) by 21 days.

This patent is subject to a terminal disclaimer.

(21) Appl. No.: 13/133,187

(22) PCT Filed: Dec. 9, 2009

(86) PCT No.: PCT/US2009/067334
§ 371 (c)(1),
(2), (4) Date: Aug. 31, 2011

(87) PCT Pub. No.: WO2010/077739
PCT Pub. Date: Jul. 8, 2010

(65) Prior Publication Data
US 2011/0305655 A1    Dec. 15, 2011

Related U.S. Application Data

(60) Provisional application No. 61/120,878, filed on Dec. 9, 2008, provisional application No. 61/120,883, filed on Dec. 9, 2008.

(51) Int. Cl.
*A61K 8/00* (2006.01)
*A61K 8/02* (2006.01)

(52) U.S. Cl.
USPC .......................................... 424/64; 424/401

(58) Field of Classification Search
None
See application file for complete search history.

(56) References Cited

U.S. PATENT DOCUMENTS

| 4,871,536 A | 10/1989 | Arraudeau et al. |
| 5,389,363 A | 2/1995 | Snyder et al. |
| 5,998,547 A | 12/1999 | Hohner |
| 6,482,400 B1 * | 11/2002 | Collin .................... 424/70.6 |
| 6,492,455 B1 | 12/2002 | Nadolsky |
| 2004/0223986 A9 | 11/2004 | Boussouira et al. |
| 2007/0031361 A1 | 2/2007 | Herrmann et al. |
| 2007/0110702 A1 | 5/2007 | Ehara |
| 2008/0207871 A1 | 8/2008 | Seiler et al. |
| 2009/0060959 A1 | 3/2009 | Igarashi |

FOREIGN PATENT DOCUMENTS

| EP | 2 036 536 | 3/2009 |
| WO | WO 96/03967 | 2/1996 |
| WO | WO 01/17485 | 3/2001 |
| WO | 2006 103879 | 10/2006 |
| WO | WO 2006/112690 | 10/2006 |
| WO | WO 2007/048672 | 5/2007 |
| WO | WO 2007/096400 | 8/2007 |
| WO | WO 2008/046763 | 4/2008 |

OTHER PUBLICATIONS

U.S. Appl. No. 13/133,179, filed Aug. 2, 2011, Bui, et al.
U.S. Appl. No. 13/132,724, filed Aug. 11, 2011, Bui, et al.
U.S. Appl. No. 13/132,811, filed Jul. 29, 2011, Bui, et al.
U.S. Appl. No. 13/140,083, filed Aug. 17, 2011, Bui, et al.
International Search Report issued Jun. 24, 2010 in PCT/US09/067334 filed Dec. 9, 2009.
Hauthal, Tenside Surf. Det. 2008, 45(1), 30-42.

* cited by examiner

*Primary Examiner* — Carlos Azpuru
*Assistant Examiner* — Casey Hagopian
(74) *Attorney, Agent, or Firm* — Oblon, Spivak, McClelland, Maier & Neustadt, L.L.P.

(57) ABSTRACT

An emulsion lip composition, in solid or stick form, comprising: (a) a reaction product of (i) at least one polyamine with (ii) an oil-soluble polar modified polymer comprising at least one C2-C20 monomer; (b) water; (c) at least one non-volatile solvent; and (d) at least one colorant; and a method of using thereof.

20 Claims, No Drawings

MOISTURIZING AND SHINE-IMPARTING EMULSION LIP COMPOSITIONS

FIELD OF THE INVENTION

The present invention generally relates to a novel moisturizing lip composition. More particularly, the present invention relates to an emulsion lip composition, such as a lipstick or lip gloss, capable of moisturizing lips due to the presence of a significant amount of water and oil contained therein and providing improved shine.

DISCUSSION OF THE BACKGROUND

The problem with conventional solid lipsticks which claim to moisturize the lips is that only small amounts of water may be incorporated therein which tends to evaporate very quickly yielding little, to no, moisturizing effect. The addition of too much water typically results in poor stick structure and pay-off. Moreover, these types of conventional solid moisturizing lipsticks require the use of surfactants in order to form the emulsion. Finally, in order to make a solid lipstick product which possesses transfer resistance properties, silicone resins are employed in order to achieve this property and the presence of water for moisturization is non-existent.

Therefore, it is an object of the present invention to provide a lip composition, preferably in stick form, containing a significant amount of water, in a stable and/or transfer-resistant emulsion, wherein the composition does not require a silicone resin or a surfactant/emulsifier, imparts a high degree of shine, hydrates the lips and/or moisturizes the lips.

SUMMARY OF THE INVENTION

The present invention relates to a lip composition comprising:
(a) at least one polyamine;
(b) at least one oil-soluble polar modified polymer;
(c) water;
(d) at least one non-volatile solvent capable of solubilizing the oil-soluble polar modified polymer;
(e) at least one colorant.
(f) optionally, at least one wax;
(g) optionally, at least one water-soluble film forming polymer; and
(h) optionally, at least one volatile oil.

The present invention relates to a lip composition comprising:
(a) a reaction product of at least one polyamine and at least one oil-soluble polar modified polymer;
(b) water;
(c) at least one non-volatile solvent capable of solubilizing the oil-soluble polar modified polymer;
(d) at least one colorant.
(e) optionally, at least one wax;
(f) optionally, at least one water-soluble film forming polymer; and
(g) optionally, at least one volatile oil.

The present invention relates to a lip composition made by combining ingredients comprising:
(a) at least one polyamine;
(b) at least one oil-soluble polar modified polymer;
(c) water;
(d) at least one non-volatile solvent capable of solubilizing the oil-soluble polar modified polymer;
(e) at least one colorant.
(f) optionally, at least one wax;
(g) optionally, at least one water-soluble film forming polymer; and
(h) optionally, at least one volatile oil.

Preferably, the composition is free of surfactants, emulsifiers and/or silicone resins.

The present invention also relates to a method of making up lips comprising applying the above-disclosed composition onto the lips.

It has been surprisingly discovered that the resultant composition, even with the presence of water therein, is stable in the absence of emulsifiers, can have good stick hardness, delivers hydration and moisture onto the lips in a comfortable manner, is easily deposited onto the lips and imparts a high degree of shine without the need for silicone fluids.

DETAILED DESCRIPTION OF THE INVENTION

"Film former" or "film forming agent" or "film forming resin" as used herein means a polymer which, after dissolution in at least one solvent (such as, for example, water and organic solvents), leaves a film on the substrate to which it is applied, for example, once the at least one solvent evaporates, absorbs and/or dissipates on the substrate.

"Tackiness", as used herein, refers to the adhesion between two substances. For example, the more tackiness there is between two substances, the more adhesion there is between the substances.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion, bending or leaning if the composition is in stick form, melting, or syneresis (or sweating). The stability is further tested by repeating the 8-week test at 37° C., 40° C., 45° C., 50° C., and under freeze-thaw conditions. A composition is considered to lack stability if in any of these tests an abnormality that impedes functioning of the composition is observed. The skilled artisan will readily recognize an abnormality that impedes functioning of a composition based on the intended application.

"Volatile", as used herein, means having a flash point of less than about 100° C.

"Non-volatile", as used herein, means having a flash point of greater than about 100° C.

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Waterproof" as used herein refers to the ability to repel water and permanence with respect to water.

Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions.

Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

Polyamine Compound

According to the present invention, compositions comprising at least one polyamine compound are provided. In accordance with the present invention, the polyamine compound has at least two primary amine groups available to react with hydrophilic groups of the oil-soluble polar modified polymer.

According to particularly preferred embodiments, the polyamine compound is a polyalkyleneimine, preferably a C2-C5 polyalkyleneamine compound, more preferably a polyethyleneimine or polypropyleneimine. Most preferably, the polyalkylenamine is polyethyleneimine ("PEI"). The polyalkyleneamine compound preferably has an average molecular weight range of from 500-200,000, including all ranges and subranges therebetween.

According to preferred embodiments, compositions of the present invention contain polyethyleneimine compounds in the form of branched polymers. Commercially available examples of such polymers are available from BASF under the tradename LUPASOL or POLYIMIN. Non-limiting examples of such polyethyleneimines include Lupasol® PS, Lupasol® PL, Lupasol® PR8515, Lupasol® G20, Lupasol® G35.

According to other embodiments of the present invention, polyamines such as polyethyleneimines and polypropyleneimines can be in the form of dendrimers. Non-limiting examples of such dendrimers are manufactured by the company DSM, and/or are disclosed in U.S. Pat. No. 5,530,092 and U.S. Pat. No. 5,610,268, the contents of which are hereby incorporated by reference. Commercially available examples of such polymers include polyamidoamine or polypropyleneimine polymers from DENDRITECH sold under the STARBURST® name.

According to other embodiments of the present invention, derivatives of polyalkyleneamines are suitable polyamines. Such derivatives include, but are not limited to, alkylated derivatives, the addition products of alkylcarboxylic acids to polyalkyleneamines, the addition products of ketones and of aldehydes to polyalkyleneamines, the addition products of isocyanates and of isothiocyanates to polyalkyleneamines, the addition products of alkylene oxide or of polyalkylene oxide block polymers to polyalkyleneamines, quaternized derivatives of polyalkyleneamines, the addition products of a silicone to polyalkyleneamines, and copolymers of dicarboxylic acid and polyalkyleneamines. Even further suitable polyamines include, but are not limited to, polyvinylimidazoles (homopolymers or copolymers), polyvinylpyridines (homopolymers or copolymers), compounds comprising vinylimidazole monomers (see, for example, U.S. Pat. No. 5,677,384, hereby incorporated by reference), and polymers based on amino acids containing a basic side chain (preferably selected from proteins and peptides comprising at least 5%, preferably at least 10% of amino acids selected from histidine, lysine and arginine). Such suitable polyamines as described above include those disclosed and described in U.S. Pat. No. 6,162,448, the contents of which are hereby incorporated by reference. Commercially available examples of such polymers include polyvinylamine/formamide such as those sold under the Lupamine® name by BASF, chitosan from vegetable origin such as those sold under the Kiosmetine® or Kitozyme® names, or copolymer 845 sold by ISP.

According to preferred embodiments, the at least one polyamine compound is present in the composition of the present invention in an amount ranging from about 0.1 to about 10% by weight, more preferably from about 0.2 to about 5% by weight, based on the total weight of the composition, including all ranges and subranges within these ranges.

Preferably, the amount of polyamine compound reacted with the oil-soluble polar modified polymer is such that at least two amine groups on the polyamine compound react with the oil-soluble polar modified polymer to form links or bonds between the amine groups and the hydrophilic groups of the oil-soluble polar modified polymer. The appropriate amount of polyamine compound to react with the oil-soluble polar modified polymer to obtain a reaction product can be easily determined, taking into account the number/amount of reactive amine groups on the polyamine compound and the number/amount of corresponding reactive groups on the oil-soluble polar modified polymer (for example, maleic anhydride groups). According to preferred embodiments, excess oil-soluble polar modified polymer (as determined by the relative number/amount of corresponding reactive groups on the polymer as compared to the reactive amine groups on the polyamine) is reacted with polyamine. Preferably, the polyamine to oil-soluble polar modified ratio is between 0.005 and 1, preferably between 0.006 and 0.5, and preferably between 0.007 and 0.1, including all ranges and subranges therebetween.

Oil-Soluble Polar Modified Polymer

According to the present invention, compositions comprising at least one oil-soluble polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, C2-C20 compounds such as, for example, styrene, ethylene, propylene, isopropylene, butylene, isobutylene, pentene, isopentene, isoprene, hexene, isohexene, decene, isodecene, and octadecene, including all ranges and subranges therebetween. Preferably, the monomers are C2-C8 compounds, more preferably C2-C6 compounds, and most preferably C2-C4 compounds such as ethylene, propylene and butylene.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to the present invention, the polar modified polymer is oil-soluble: that is, the polymer does not contain a sufficient amount of hydrophilic unit(s) to render the entire polymer water-soluble or oil-insoluble. According to preferred embodiments, the polar modified polymer contains the same amount of hydrophobic monomer as hydrophilic unit (1:1 ratio) or more hydrophobic monomer than hydrophilic unit. According to particularly preferred embodiments, the polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the polar modified polymer is a wax. According to particularly preferred embodiments, the polar modified wax is made via metallocene catalysis, and includes polar groups or units as well as a hydrophobic backbone. Suitable modified waxes include those disclosed in U.S. patent application publication no. 20070031361, the entire contents of which is hereby incorporated by reference. Particularly preferred polar modified waxes are C2-C3 polar modified waxes.

In accordance with preferred embodiments of the present invention, the polar modified wax is based upon a homopolymer and/or copolymer wax of hydrophobic monomers and has a weight-average molecular weight Mw of less than or equal to 25,000 g/mol, preferably of 1000 to 22,000 g/mol and particularly preferably of 4000 to 20,000 g/mol, a number-average molecular weight Mn of less than or equal to 15,000 g/mol, preferably of 500 to 12,000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Polar modified waxes can be produced in a known manner from the hompopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the C2-C3 wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred C2-C3 polar modified waxes for use in the present invention are polypropylene and/or polyethylene-maleic anhydride modified waxes ("PEMA," "PPMA," "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; Drop Point, Mettler: 106° C.) from Honeywell, A-C 596 A (PROPYLENE-MALEIC ANHYDRIDE COPOLYMER; Drop Point, Mettler: 143° C.) from Honeywell, A-C 597 (PROPYLENE-MALEIC ANHYDRIDE COPOLYMER; Drop Point, Mettler: 141° C.) from Honeywell, ZeMac® copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemcial Co., poly (ethylene-co-butyl acrylate-co-maleic anhydride) sold under the trade name of Lotader (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the Lotader name, and isobutylene maleic anhydride copolymer sold under the name ACO-5013 by ISP.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orientation (for example, atactic, isotactic or syndiotactic along the backbone).

Preferably, the polar modified polymer(s) represent from about 1% to about 30% of the total weight of the composition, more preferably from about 3% to about 20% of the total weight of the composition, and most preferably from about 5% to about 15%, including all ranges and subranges therebetween.

Non-Volatile Oil for Oil-Soluble Polar Modified Polymer

The cosmetic compositions of the present invention comprise at least one non-volatile oil capable of solubilizing the oil-soluble polar modified polymer. As used herein, the term "non-volatile" means having a boiling point of greater than about 100° C.

Examples of hydrocarbon oils which may be used include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

Further, examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

$C_8$ to $C_{26}$ fatty alcohols, for instance oleyl alcohol; and mixtures thereof.

The at least one non-volatile oil is present in the cosmetic composition of the invention in an amount of from about 1% to about 15% by weight, such as from about 1.5% to about 10% by weight, such as from about 2% to about 5% by weight, including all ranges and subranges therebetween, all weights being based on the total weight of the composition.

Water

The composition of the present invention also contains water. The water can hydrate and/or moisturize the lips after application. Water is typically present in an amount of from about 0.1% to about 50% by weight, such as from about 1% to about 40% by weight, such as from about 10% to about 30% by weight, including all ranges and subranges therebetween, all weights being based on the total weight of the composition.

Reaction Product

According to preferred embodiments of the present invention, the oil-soluble polar modified polymer is reacted with the polyamine compound, in the presence of water in, at minimum, an amount sufficient to solubilize the polyamine, to form a reaction product. In accordance with the preferred embodiments, the reaction product is water-insoluble.

Although not wanting to be bound by any particular theory, it is believed that at a temperature below 100° C., the reaction of the oil-soluble polar modified polymer with the primary amine group of the polyamine opens the anhydride ring to form a half acid and half amide crosslinked product. However, at a temperature above 100° C., the reaction of the oil-soluble polar modified polymer with the primary amine group of the polyamine opens the anhydride ring to form an imide crosslinked product. The former product is preferred over the latter product. It is not necessary for all amine groups and all hydrophilic groups to react with each other to form the reaction product. Rather, it is possible that the composition may contain free polyamine and/or free oil-soluble polar modified polymer in addition to the reaction product.

Although not wanting to be bound by any particular theory, it is also believed that the polyamine(s) can be non-covalently assembled with the polar modified polymer(s) by electrostatic interaction between an amine group of the polyamine and a hydrophilic group (for example, carboxylic acid group associated with maleic anhydride groups) of the polar modified polymer to form a supramolecule. For example, with specific reference to maleic anhydride groups, in the presence of water these groups can open to form dicarboxylic acid groups which can interact with protonated primary amines of the polyamine through ionic interaction to form a polymer-polymer complex with hydrophilic core crosslinkers and a hydrophobic network that act as supramolecular capsule. If a large amount of maleic anhydride groups are present, the secondary amine groups of polyamine are also protonated and interact with alkyl carboxylates.

According to preferred embodiments, the oil-soluble polar modified polymer is in an oil carrier, and the polyamine compound is in an aqueous carrier, and the reaction occurs by combining the oil carrier and the aqueous carrier. Because the oil-soluble polar modified polymer is typically solid at room temperature, the oil carrier is preferably heated to liquefy the polymer prior to combination with the aqueous carrier. Preferably, the oil carrier is heated beyond the melting point of the oil-soluble polar modified polymer, typically up to about 80° C., 90° C. or 100° C.

Without intending to be bound by any particular theory, it is believed that the reason for this is that due to the chemical and physical reactions which take place when the oil-soluble polar modified polymer is combined with the polyamine, the subsequent reaction product that is formed is surprisingly and unexpectedly able to entrap large amounts of water molecules within its hydrophobic matrix. The resultant product is eminently capable of forming a film, is self-emulsifying, waterproof. Moreover, the product is both stable and capable of carrying various types of ingredients.

Wax

The composition of the present invention optionally includes the presence of at least one wax compatible with the composition. If a wax is present, the wax helps improve or increase transfer-resistance of the composition. As used herein, "wax" may be any lipophilic fatty compound. Non-limiting examples of suitable waxes include waxes of natural origin such as beeswax, carnauba wax, candelilla wax, ouricury wax, Japan wax, cork fiber wax, paraffin wax, microcrystalline wax, sugar cane wax, lignite wax, montan wax, hydrogenated oils, waxes of synthetic origin, and the like.

In general, the wax, if present, is present in the composition in an amount of from about 5 to about 25% by weight, such as from about 8 to about 20% by weight, and from about 10 to about 15% by weight, including all ranges and subranges therebetween, all weights being based on the total weight of the composition.

Water Soluble Film Forming Polymer

The composition of present invention optionally includes the presence of at least one water-soluble film forming agent. If a water-soluble film forming polymer is present, the polymer helps improve or increase transfer-resistance of the composition. The term "water-soluble or water-dispersible" is understood to mean polymers having a solubility in water, measured at 25° C., at least equal to 0.1 gram/liter (g/l) (preparation of a macroscopically isotropic and transparent solution which may or may not be colored). This solubility is preferably greater than or equal to 1 g/l. Like the other compounds, these polymers had to be physiologically acceptable, that is to say compatible with the skin, mucous membranes, hair and scalp.

The term "film-forming polymer" is understood to mean a polymer capable of forming, by itself alone or in the presence of an additional agent which is able to form a film, a continuous film and preferably a film having a cohesion and mechanical properties such that the film can be isolated from a support.

The film-forming polymers can be chosen, for example, from: vinyl polymers, such as polyvinyl acetate, polyvinylpyrrolidones, copolymers of methyl vinyl ether and of maleic anhydride, the copolymer of vinyl acetate and of crotonic acid, copolymers of vinylpyrrolidone and of vinyl acetate, copolymers of vinylpyrrolidone and of caprolactam, or polyvinyl alcohols; film-forming cellulose derivatives, such as hydroxyethylcellulose, hydroxypropylcellulose, hydroxypropylmethylcellulose, methylcellulose, ethylhydroxyethylcellulose, carboxymethylcellulose and quaternized cellulose derivatives; starches and their derivatives; optionally modified polymers of natural origin, such as pullulan, pectin, mannan, galactomannans, glucomannans and their derivatives, gum arabic, guar gum, xanthan gum, karaya gum; alginates, carrageenans, ulvans and other algal colloids; hyaluronic acid and its derivatives; shellac, sandarac gum, dammars, elemis, copals; deoxyribonucleic acid; mucopolysaccharides, such as hyaluronic acid, chondroitin sulphate; anionic, cationic, amphoteric or nonionic polymers derived from chitin or from chitosan; protein polymers, such as wheat or soybean protein; keratin and its derivatives, for example keratin hydrolysates and sulphonic keratins; casein; albumin; collagen; glutelin; glucagon; gluten; zein; gelatins and their derivatives; acrylic copolymers of phosphorylcholine, such as poly[2-(methacryloyloxyethyl)phosphorylcholine], sold under the name Lipidure HM by NOF Corporation (INCI name: Polyphosphorylcholine glycol acrylate); anion-cation complexes of gum arabic/gelatin or gum arabic/chitosan or collagen/glycosoaminoglycan type; and the mixtures of these polymers.

According to a preferred embodiment of the invention, the film-forming polymer is chosen from vinyl polymers, cellulose derivatives and their mixtures.

Non-limited examples thereof include polyvinyl pyrrolidone, polyvinyl alcohol, and mixtures thereof.

In general, the at least one water soluble film forming polymer, if present, is present in the composition in an amount of from about 1 to about 15% by weight, such as from about 2 to about 10% by weight, and from about 3 to about 5% by weight, including all ranges and subranges therebetween, all weights based on the total weight of the composition.

Volatile Solvent

The composition of present invention optionally includes the presence of at least one volatile solvent. If a volatile solvent is present, the solvent helps improve or increase transfer-resistance of the composition through evaporation. If present, the at least one volatile oil may preferably be chosen from a volatile silicone oil or a volatile non-silicone oil.

Suitable volatile silicone oils include, but are not limited to, linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Suitable volatile non-silicone oils may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane and for example, the oils sold under the trade names of Isopar or Permethyl. Preferably, the volatile non-silicone oils have a flash point of at least 40° C.

Non-limiting examples of volatile non-silicone oils are listed in Table 2 below.

TABLE 2

| Compound | Flash Point (° C.) |
| --- | --- |
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin C11-C13) | 62 |
| Isopar H (isoparaffin C11-C12) | 56 |

In general, the at least one volatile solvent is present in the composition in an amount of from about 20 to about 70% by weight, such as from about 30 to about 60% by weight, and from about 40 to about 50% by weight, including all ranges and subranges therebetween, all weights being based on the total weight of the composition.

Colorant

The composition of the present invention may also contain at least one colorant, such as a pigment or dyestuff. Examples of suitable pigments include, but are not limited to, inorganic pigments, organic pigments, lakes, pearlescent pigments, irridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No.3 (CI 45,430) and the dye or lakes based on cochineal carmine (CI 75,570) and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the cosmetic compositions of the invention will depend on the color, intensity and use of the cosmetic composition and, as a result, will be determined by those skilled in the art of cosmetic formulation.

Optional Ingredients

The composition of the present invention may also include any one, or more, optional ingredients. Examples thereof include, but are not limited to, co-solvents, plasticizers, preservatives, fillers, active ingredients and sunscreens.

It has surprisingly been discovered that the composition of the present invention forms a stable, transfer resistant emulsion, in solid or stick form, without the need for having to employ silicone resin and a surfactant to form the emulsion. Without intending to be bound by theory, it is believed that the combination of the polyamine and oil-soluble polar modified polymer forms a matrix capable of entrapping the water and oil emulsion. Consequently, when the composition is applied onto the lips the water, rather than immediately evaporating from the surface of the lips, thereby imparting no further hydration/moisturizing properties, instead remains within the matrix until it is released therefrom by the friction caused by a consumer when their lips come together during the normal course of the day. As a result, hydrating/moisturizing water is released onto the surface of the lips over a prolonged period of time. Moreover, while the product imparts continuous moisturization onto the lips, a feeling of dryness is not experienced by the lips during, or after evaporation of the solvent from the lips. This is particularly surprising and unexpected in transfer-resistant cosmetic products.

It has also surprisingly been discovered that the composition of the present invention forms a stable emulsion, in solid or stick form, without the need for having to employ a surfactant to form the emulsion by the same mechanism described above.

It also has surprisingly been discovered that the composition of the present invention delivers a shine upon applied on the lips without the need for having to employ silicone fluids.

The composition of the present invention preferably possesses a hardness value of from about 40 to about 200, such as from about 70 to about 150, and from about 80 to about 120 gram force.

This hardness is measured in one of two ways. A first test for hardness is according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ☐ 50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 200 gf, such as from 30 gf to 150 gf, for a sample of 8.1 mm in diameter stick, and further such as from 50 gf to 200 gf, and also further such as from 50 gf to 150 gf for a sample of 12.7 mm in diameter stick.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within preferred embodiments of the invention.

The present invention is further described in terms of the following non-limiting examples. Unless otherwise indicated, all parts and percentages are on a weight-by-weight percentage basis.

EXAMPLE 1

Moisturizing Emulsion Lip Stick

| Phase | INCI Name | Wt |
|---|---|---|
| A1 | Polyglyceryl-2-Triisostearate | 3 |
| A1 | Octyldodecyl Neopantanoate | 15.0 |
| A1 | Hydrogenated Polydecene | Q.S. |
| A1 | Polypropylene-ethylene-maleic anhydride copolymer | 7 |
| A1 | Isohexadecane | 2.33 |
| A1 | Polyethylene | 8 |
| A1 | Pigments | 5 |
| A1 | Tricaprylin | 13.8 |
| A1 | Mica | 2 |
| B1 | Deionized Water | 22.50 |
| B1 | b-Polyethyleneimine (50% SOLID/50% WATER) | 0.25 |
| B1 | Glycerin | 3 |
| | Total | 100 |

Procedure:
1. Heated all the oils of phase A in a Beaker 1 at 95 Celsius degrees.
2. Added the Licocare PP207 into beaker 1 containing the oils to dissolve.
3. When the licocare PP207 was totally dissolved, added the wax and pigments into beaker 1 and stirred well until wax was dispersed.
4. Reduced the temperature of beaker 1 to 85 Celsius degrees.
5. Used the Silverson to mix the phase A content in beaker 1 while maintaining the temperature at 85 Celsius degrees.
6. In a separate beaker 2, added the Lupasol G-35 into hot water at 85 Celsius degrees and stirred well.
7. Added dropwise the Lupasol G-35 solution into the beaker 1 while the speed of Silversion was increased to 9000 rpm.
8. Left Silverson @ 9000 rpm for 30 minutes, after that reduced speed to 2000 rpm for 5 minutes.
9. Poured mixture at 80 C into lipstick molds. Cooled for 20 minutes in refrigerator.

EXAMPLE 2

Moisturizing and Shiny Emulsion Lip Stick

| Phase | Chemical Name | % wt/wt |
|---|---|---|
| A | Octododecanol | 10.50 |
| A | Octyldodecyl Neopantanoate | 10.00 |
| A | HYDROGENATED POLYISOBUTENE | QS |
| A | POLYBUTENE | 5.00 |
| A | Polypropylene-ethylene-maleic acid anhydride copolymer wax | 7.00 |
| A | Isohexadecane | 3.00 |
| A | Polyethylene | 8.00 |
| A | Ozokerite | 0.50 |
| A | VP/Eicosene Copolymer | 3.00 |
| A | Pigments + Titanium dioxide | 6.97 |
| B | Deionized Water | 15.00 |
| B | b-Polyethyleneimine (50% SOLID/50% WATER) | 0.25 |
| B | Glycerin | 3.00 |
| B | Caprylic Glycol | 0.25 |
| B | Pentylene Glycol | 1.00 |

Procedure
1. Materials identified as phase A were added to a suitable size beaker A and heated to 95 Celsius degrees.
2. When enough solids had melted, the contents were mixed with moderate speed until all solids had melted at 95 Celsius degrees.
3. The temperature of the contents of main beaker A was slightly lowered to 85-90 Celsius degrees.
4. In a separate beaker B, materials identified as phase B were added and heated to 85 Celsius degrees with moderate mixing.
5. The contents of side beaker B was added dropwise into the beaker A while emulsifying at 1300 rpm under the VMI Turbo text mixer for 26 minutes.
6. The contents were poured into lipstick molds at 87 Celsius degrees.
7. The lipstick in molds was placed in a cooling tunnel for 15 minutes at −10 Celsius degrees. Once cooled, the lipstick in molds were removed from the cooling tunnel to equilibrate to 25 Celsius degrees and removed from mold after lipsticks had thawed to 25 Celsius degree.

EXAMPLE 3

Long Wear and Transfer Resistant Emulsion Lip Stick

| Phase | INCI Name | Wt/wt % |
|---|---|---|
| A1 | Isododecane | Q.S. |
| A1 | Polyvinyl Pyrrolidone | 3.00 |
| A1 | Licocare PP207 | 5.00 |
| A1 | Synthetic Beeswax | 3.00 |
| A1 | Polyethylene | 10 |
| A1 | Pigments | 5.0 |
| A3 | Mica | 2.00 |
| B1 | Deionized Water | 30 |
| B1 | b-Polyethyleneimine (50% solid/50% water) | 0.25 |
| | Total | 100 |

Procedure:
1. Heated all the oils of phase A in a Beaker 1 at 95 Celsius degrees.
2. Added the Licocare PP207 into beaker 1 containing the oils to dissolve.
3. When the licocare PP207 was totally dissolved, added Polyvinyl Pyrrolidone and stirred until the solution was homogeneous.
4. Added the wax and pigment grind A2 into beaker 1 and stirred well until wax was dispersed.

5. Reduced the temperature of beaker 1 to 85 Celsius degrees.
6. Used the Silverson to mix the phase A content in beaker 1 while maintaining the temperature at 85-90 Celsius degrees.
7. In a separate beaker 2, added the Lupasol G-35 into hot water at 85 Celsius degrees and stirred well.
8. Added dropwise the Lupasol G-35 solution into the beaker A while the speed of Silversion was increased to 9000 rpm.
9. Left Silverson @ 9000 rpm for 30 minutes, after that reduced speed to 2000 rpm for 5 mins.

Poured mixture at 85-90 C into molds. Cooled 20 minutes in refrigerator.

EXAMPLE 4

Long Wear and Transfer Resistant Emulsion Lip Stick

| Phase | Chemical Name | % wt/wt |
|---|---|---|
| A | Sucrose Acetate Isobutyrate | 3.00 |
| A | Polypropylene-ethylene-maleic acid anhydride copolymer wax | 7.00 |
| A | Isohexadecane | 3.00 |
| A | VP/Eicosene Copolymer | 3.00 |
| A | Polyethylene | 10.00 |
| A | Ozokerite | 0.50 |
| A | Pigments + Titanium dioxide | 6.97 |
| A | Isododecane | Q.S. |
| B | Deionized Water | 15.00 |
| B | b-Polyethyleneimine (50% solid/50% water) | 0.25 |
| B | Glycerin | 3.00 |

Procedure
1. Materials identified as phase A were added to a suitable size beaker A and heated to 95 Celsius degrees.
2. When enough solids had melted, the contents were mixed with moderate speed until all solids had melted at 95 Celsius degrees.
3. The temperature of the contents of main beaker A was slightly lowered to 85-90 Celsius degrees.
4. In a separate beaker B, materials identified as phase B were added and heated to 85 Celsius degrees with moderate mixing.
5. The contents of side beaker B was added dropwise into the beaker A while emulsifying at 1300 rpm under the VMI Turbo text mixer for 26 minutes.
6. The contents were poured into lipstick molds at 87 Celsius degrees.
7. The lipstick in molds was placed in a cooling tunnel for 15 minutes at −10 Celsius degrees. Once cooled, the lipstick in molds were removed from the cooling tunnel to equilibrate to 25 Celsius degrees and removed from mold after lipsticks had thawed to 25 Celsius degrees.

EXAMPLE 5

Moisturizing and Glossy Emulsion Lipgloss

| Phase | Chemical Name | % wt/wt |
|---|---|---|
| A | Octododecanol | 9.00 |
| A | Octyldodecyl Neopantanoate | 3.00 |
| A | HYDROGENATED POLYISOBUTENE | Q.S. |
| A | POLYBUTENE | 13.15 |
| A | Polypropylene-ethylene-maleic acid anhydride copolymer wax | 10.00 |
| A | Isohexadecane | 3.33 |
| A | Lauroyl Lysine | 0.20 |
| A | ALUMINUM STARCH OCTENYLSUCCINATE | 1.00 |
| A | VP/Eicosene Copolymer | 3.50 |
| A | Pigment | 0.77 |
| B | Deionized Water | 40.00 |
| B | b-Polyethyleneimine (50% solid/50% water) | 0.30 |
| B | Caprylic Glycol | 0.25 |
| B | Glycerin | 3.00 |
| B | Pentylene Glycol | 1.00 |

Procedure
1. Materials identified as phase A were added to a suitable size beaker A and heated to 95 Celsius degrees.
2. When enough solids had melted, the contents were mixed with moderate speed until all solids had melted at 95 Celsius degrees.
3. The temperature of the contents of main beaker A was slightly lowered to 85-90 Celsius degrees.
4. In a separate beaker B, materials identified as phase B were added and heated to 85 Celsius degrees with moderate mixing.
5. The contents of side beaker B was added dropwise into the beaker A while emulsifying at 1300 rpm under the VMI Turbo text mixer for 26 minutes.
6. The contents were cooled to 25 Celsius degrees with a propeller blade mixing at 150 rpm.

EXAMPLE 6

Long Wear Emulsion Lip Color

| Phase | Chemical Name | Wt/wt % |
|---|---|---|
| A | Polypropylene-ethylene-maleic acid anhydride copolymer wax | 10 |
| A | Octododecanol | 5 |
| A | Iron Oxide (and) mica | 5 |
| A | isohexadecane | Q.S. |
| B | Water | 50.0 |
| B | Iron Oxide (and) mica | 5 |
| B | b-Polyethyleneimine (50% solid/50% water) | 0.20 |

Procedure
1. Materials identified as phase A were added to a suitable size beaker A and heated to 70 Celsius degrees.
2. When enough solids had melted, the contents were mixed with moderate speed until all solids had melted at 70 Celsius degrees.
3. In a separate beaker B, materials identified as phase B were added and heated to 70 Celsius degrees with moderate mixing.
4. The contents of side beaker B was added dropwise into the beaker A while mixing at 400 rpm under the VMI Turbo text mixer for 5 minutes.
5. The contents were cooled to 25 Celsius degrees with a propeller blade mixing at 150 rpm.

TABLE 1

Shearing test of emulsion lip sticks in Example 1, 2, 3, 4

|  | Example 1 | Example 2 | Example 3 | Example 4 |
|---|---|---|---|---|
| Gram Force | 74 | 72 | 98 | 42 |

TABLE 2

Shine kinetics for Shiny emulsion Lipstick in Example 2

| n = 6 | Initial Shine | 1 hr shine | 2 hr Shine |
|---|---|---|---|
| Example 2 | 144 ± (19.4) | 129.8 ± (17.0) | 116.7 ± (20.2) |

What is claimed is:

1. An emulsion lip composition, in solid or stick form, comprising:
   (a) a reaction product of (i) at least one polyamine with (ii) an oil-soluble polar modified polymer comprising at least one C2-C20 monomer;
   (b) water;
   (c) at least one non-volatile solvent; and
   (d) at least one colorant.

2. The composition of claim 1, wherein the composition is free of silicone resin, surfactant and/or emulsifier.

3. The composition of claim 1, wherein the composition further comprises at least one wax, at least one water soluble film forming polymer and at least one volatile oil.

4. The composition of claim 1, wherein the polyamine is branched polyethyleneimine.

5. The composition claim 1, wherein the composition is made using from 0.05 to 5% by weight, based on the weight of the composition, of the polyamine.

6. The composition of claim 1, wherein the composition is made using from 3 to 30% by weight, based on the weight of the composition, of the polar modified polymer.

7. The composition claim 3, wherein the composition is made using from 0.05 to 5% by weight, based on the weight of the composition, of the polyamine.

8. The composition of claim 3, wherein the composition is made using from 3 to 30% by weight, based on the weight of the composition, of the polar modified polymer.

9. The composition of claim 1, wherein water is present in an amount of from 0.1 to 50% by weight, based on the weight of the composition.

10. The composition of claim 3, wherein water is present in an amount of from 0.1 to 50% by weight, based on the weight of the composition.

11. The composition of claim 1, wherein the non-volatile solvent is a non-volatile oil.

12. The composition of claim 3, wherein the water soluble film forming polymer is selected from the group consisting of polyvinyl pyrolidone, polyvinyl alcohol, and mixtures thereof.

13. The composition of claim 3, wherein the water soluble film forming polymer is present in an amount of from 1 to 15% by weight, based on the weight of the composition.

14. The composition of claim 3, wherein the volatile oil is selected from the group consisting of isododecane, undecane, tridecane, and mixtures thereof.

15. The composition of claim 3, wherein the volatile oil is present in an amount of from 20 to 70% by weight, based on the weight of the composition.

16. The composition of claim 1, wherein the composition has a hardness value of from about 30 to about 200 gram-force.

17. The composition of claim 1, wherein the oil-soluble polar modified polymer comprises at least one C2-C4 monomer, is modified with at least one hydrophilic unit, has a weight-average molecular weight of less than or equal to 25 000 g/mol and has a melting point above 75° C.

18. The composition of claim 17, wherein the polyamine is branched polyethyleneimine.

19. The composition of claim 3, wherein the oil-soluble polar modified polymer comprises at least one C2-C4 monomer, is modified with at least one maleic anhydride group, has a weight-average molecular weight of less than or equal to 25 000 g/mol and has a melting point above 75° C.

20. A method of making-up lips comprising applying onto the lips the composition of claim 1.

* * * * *

UNITED STATES PATENT AND TRADEMARK OFFICE
CERTIFICATE OF CORRECTION

| | |
|---|---|
| PATENT NO. | : 8,551,461 B2 |
| APPLICATION NO. | : 13/133187 |
| DATED | : October 8, 2013 |
| INVENTOR(S) | : Hy S. Bui et al. |

It is certified that error appears in the above-identified patent and that said Letters Patent is hereby corrected as shown below:

In the Claims

Column 17, line 34, "The composition claim 1," should read --The composition of claim 1,--;

line 39, "The composition claim 3," should read --The composition of claim 3,--.

Signed and Sealed this
Eighteenth Day of February, 2014

Michelle K. Lee
*Deputy Director of the United States Patent and Trademark Office*